(12) United States Patent
Corvi Mora et al.

(10) Patent No.: US 6,649,658 B1
(45) Date of Patent: Nov. 18, 2003

(54) (−)-VERBENONE DERIVATIVES

(75) Inventors: Paolo Corvi Mora, Piacenza (IT); Angelo Ranise, Genoa (IT)

(73) Assignee: Euphar Group SRL, Milan (IT)

( * ) Notice: Subject to any disclaimer, the term of this patent is extended or adjusted under 35 U.S.C. 154(b) by 0 days.

(21) Appl. No.: 09/958,998

(22) PCT Filed: Apr. 13, 2000

(86) PCT No.: PCT/EP00/03339
§ 371 (c)(1),
(2), (4) Date: Oct. 15, 2001

(87) PCT Pub. No.: WO00/63159
PCT Pub. Date: Oct. 26, 2000

(30) Foreign Application Priority Data

Apr. 16, 1999 (IT) .......................... MI99A0799

(51) Int. Cl.[7] ..................... A61K 31/15; A61K 31/40; A61K 31/435; C07C 249/00; C07D 207/30
(52) U.S. Cl. ................ 514/640; 514/661; 514/429; 514/277; 514/231.2; 564/253; 564/460; 548/560; 546/1; 544/106
(58) Field of Search ............... 564/253, 460; 514/640, 661, 429, 277, 231.2; 548/560; 546/1; 544/106

(56) References Cited

U.S. PATENT DOCUMENTS

| 4,157,451 A | * | 6/1979 | Ohloff et al. ............... 569/875 |
| 4,190,675 A | * | 2/1980 | Vegezzi ..................... 424/331 |
| 4,876,276 A | * | 10/1989 | Mechoulam et al. ....... 514/454 |
| 5,478,821 A | * | 12/1995 | Bloy et al. ................. 514/210 |
| 5,532,277 A | * | 7/1996 | Janzen et al. .............. 514/579 |

OTHER PUBLICATIONS

CA 125:58781, Toda, Fumio, 1996.*
CA 120:134874, Oprean, Ioan et al, 1994.*
CA: 118: 197831, Kizlink, Juraj et al, 1993.*

* cited by examiner

Primary Examiner—Deborah C. Lambkin
(74) Attorney, Agent, or Firm—Perkins Coie LLP

(57) ABSTRACT

A description is given here of novel solid and stable derivatives of (−)-verbenone having formula (I) wherein, when X=O Z=H, =CHAr, =C(OH)COOEt, =NOR; Y=H, $NH_2$, $NH_3^+X_1^-$, NHCOAr, NHCOR, NHCONHR, NHCONHAr, $X_1^-$=pharmaceutically acceptable anion; Ar-aryl or heteroaryl, preferably phenyl, 4-chlorophenyl, 2-furyl, 2-thienyl, 2-hydroxyphenyl, 2-acetoxyphenyl; R=H, $C_1$–$C_4$ alkyl, $C_4$–$C_6$ cycloalkyl, $CH_2COOH$, $CH_2COOEt$, $CH_2COCH_3$, $CH_2CN$, $CH_2COCH_2COOEt$, $CH_2C_6H_5$; and, when X=dimethylamino, diethylamino, pyrrolidino, piperidino or morpholino: Y=H; Z=H, CONHAr, COHNR; Ar=aryl, preferably phenyl; R=H, $C_1$–$C_4$ alkyl, $C_4$–$C_6$ cycloalkyl. A description is also given of the processes for the preparation of these derivatives and of the novel intermediates used in those processes. The novel derivatives are characterized by their solubility in water; some of them also have a high anti-inflammatory activity.

25 Claims, 1 Drawing Sheet

SCHEME 1
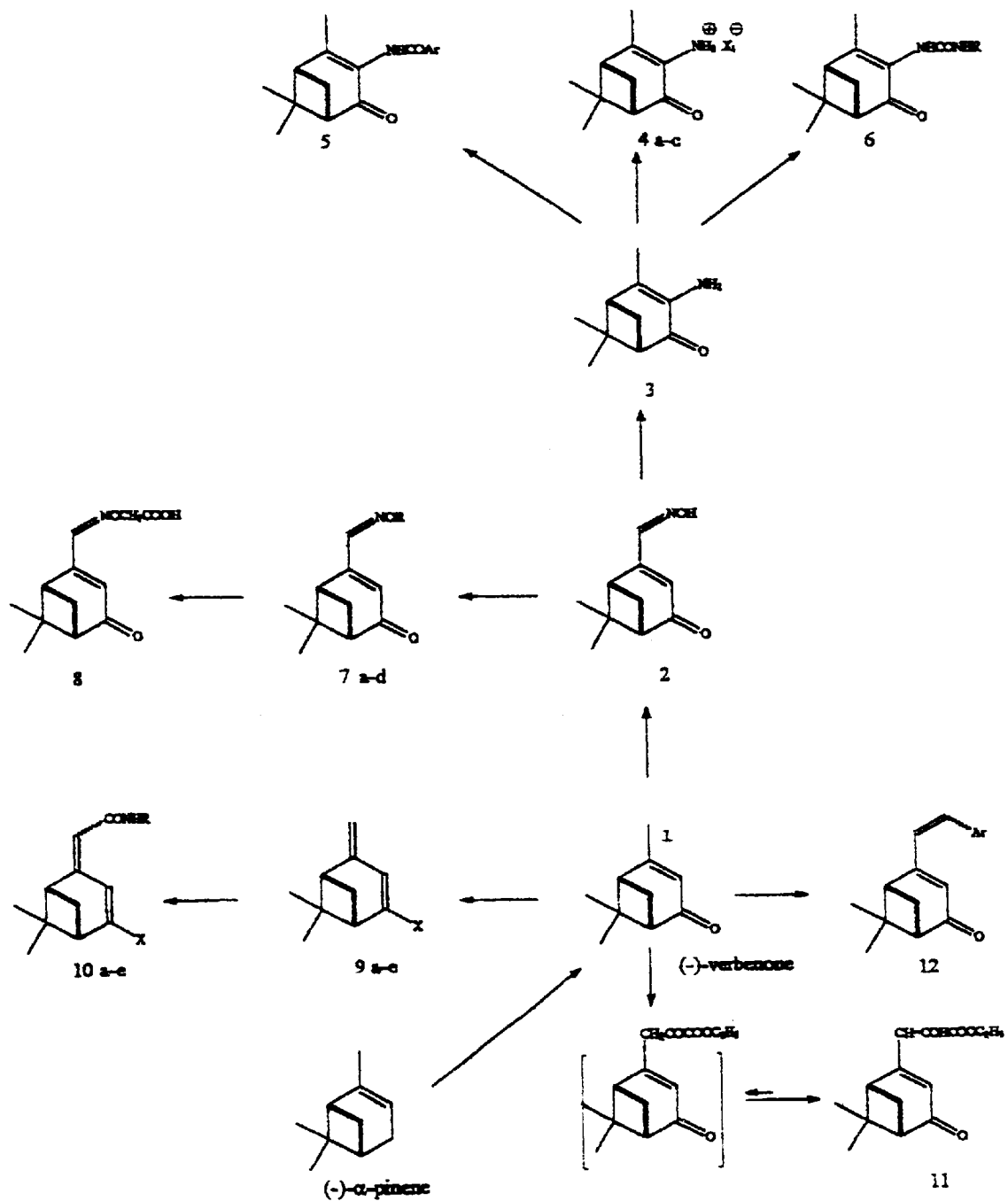

(−)-VERBENONE DERIVATIVES

This application is a 371 of PCT/EP00/03339 Apr. 13, 2000.

The present invention relates to novel derivatives of (1S,5S)-4,6,6-trimethylbicyclo[3.1.1]hept-3-en-2-one), which is more commonly known as (−)-verbenone.

The oxidation of α- and β-pinene leads to complex mixtures of monoterpenoid compounds, which are predominantly characterized by alcohol and carbonyl functions; these mixtures have been used for some time, for example in Italy (OZOPULMIN®), France (OZOTHENE®) and Germany (OZOTHIN®), in the therapy of respiratory disorders, owing to their recognised balsamic, bronchosecretolytic and antiseptic properties.

Among the above-mentioned monoterpene derivatives of the carbonyl type (−)-verbenone, a ketone derivative having an α-pinane structure whose structural formula is given below, is of particular interest.

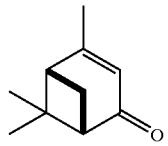

(−)-verbenone is characterized by its particular pulmonary tropism, its anti-inflammatory action on the respiratory tract and by its good muco-regulatory capacity.

The anti-inflammatory activity on the respiratory apparatus has been investigated in a series of classical experimental pharmacology tests: carrageenan- and dextran-induced oedema, adjuvant arthritis (rat), passive cutaneous anaphylaxis (rabbit), turpentine- and carrageenin-induced pleurisy (rat) and acrolein-induced aerosol (guinea pig).

(−)-verbenone is an oily substance having a characteristic odour and a boiling point of 227–228° C. d=0.975, $n_D^{20}$=1.497 and a specific rotatory power which varies according to the respective suppliers (ACROS catalogue, purity 94%: −193°, c=10, ethanol; FLUKA catalogue, purity ≧99%: 180±2°, c=10, ethanol).

However, the oily nature, the instability over time and the water-insolubility of (−)-verbenone make it difficult to administer in water-soluble dosage forms. Therefore, the object of the present invention is to synthesize (−)-verbenone derivatives that are in a solid, water-soluble form or which can in any case be readily converted into water-soluble compounds, while maintaining and possibly increasing the anti-inflammatory characteristics in respect of the respiratory tract which are typical of (−)-verbenone.

Novel pharmacologically active derivatives of (−)-verbenone having the general formula I given below:

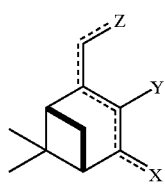

I wherein, when X=O
Z=H, =CHAR, =C(OH)COOEt, =NOR;
Y=H, $NH_2$, $NH_3^+X_1^-$, NHCOAr, NHCOR, NHCONHR, NHCONHAr,
$X_1^-$=pharmaceutically acceptable anion;
Ar=aryl or heteroaryl, preferably phenyl, 4chlorophenyl, 2-furyl, 2-thienyl, 2-hydroxyphenyl, 2-acetoxyphenyl;
R=H, $C_1$–$C_4$ alkyl, $C_4$–$C_6$ cycloalkyl, $CH_2COOH$, $CH_2COOEt$, $CH_2COCH_3$, $CH_2CN$, $CH_2COCH_2COOEt$, $CH_2C_6H_5$;
with the proviso that when X=O and Y=H, Z is other than H;
and, when X=dimethylamino, diethylamino, pyrrolidino, piperidino or morpholino:
Y=H;
Z=H, CONAr, CONHR;
Ar=aryl, preferably phenyl;
R=H, $C_1$–$C_4$ alkyl, $C_4$–$C_6$ Cyclalkyl
with the proviso that when Z=H, X is other than pyrrolidino have now been found, and form subject-matter of the present invention.

The broken line given in the general formula I is thus intended to indicate two distinct structures resulting from the different positioning of the two conjugated double bonds of (−)-verbenone, as is demonstrated more clearly by the general formulae II and III given below:

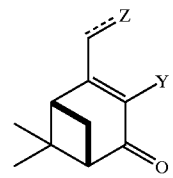

II wherein:
when Y=H, preferably Z==CHAr, =C(OH)COOEt, =NOR (that is to say, the Z group and the C-10 are joined by a double bond); or, alternatively,
when Z=H, preferably Y=$NH_2$, $NH_3^+X_1^-$, NHCOAr, NHCOR, NHCONH; and wherein:
$X_1^-$=5-sulphosalicylate, tare, 10camphosulphonate;
Ar=phenyl, 4chlorophenyl, 2-furyl, 2-thienyl, 2-hydroxyphenyl, 2-acetoxyphenyl;
R=H, $C_1$–$C_4$alkyl, $C_4$–$C_6$ cycloalkyl, $CH_2COOH$, $CH_2COOEt$, $CH_2COCH_3$, $CH_2CN$, $CH_2COCH_2COOEt$, $CH_2C_6H_5$;

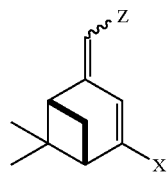

III wherein:
X=dimethylamino, diethylamino, pyrrolidino, piperidino or morpholino;
Z=H, CONHAr, CONHR;
Ar=phenyl;
R=H, methyl, cyclohexyl.

The structure II preserves the α-β-unsaturated carbonyl system typical of verbenone, while III is structurally related to the non-isolatable dienol form of verbenone A

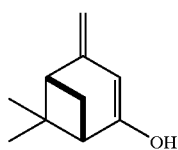

A which may, however, constitute the reactive intermediate in some reactions described here.

As will be appreciated from the accompanying Examples, the novel derivatives of (–)-verbenone according to the present invention are nearly all solid and stable at room temperature and thus can be readily used for the preparation of pharmaceutical compositions which are easy to use, preserve and administer, some of them also have an anti-inflammatory activity which is comparable to, if not higher than, that of (–)-verbenone.

The present invention therefore relates secondly to the pharmaceutical compositions containing at least one of the novel derivatives according to the present invention as active ingredient together with the excipients and/or co-adjuvants known in the art; these formulations are preferably administrable orally, parentally and topically. Among the novel (–)-verbenone derivatives of formula I, those of greatest interest are represented by formula IV, given below,

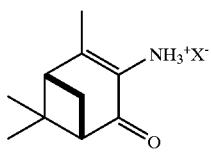

IV wherein $X_1^-$ represents, as described above, a pharmaceutically acceptable anion and, preferably, 5-sulphosalicylate, tartrate, 10-camphosulphonate. These derivatives, in addition to being completely soluble in water, have a pharmacological activity which is surprisingly higher than that of (–)-verbenone; they therefore constitute the aspect of the present invention of greatest interest.

The novel derivatives according to the present invention are readily synthesised from (–)-verbenone which, in turn, can be readily prepared firm (–)-α-pinene; in particular, it has been observed that the best pharmacological results are obtained by using as starting material (–)-verbenone having a high degree of optical purity, preferably of at least –180°, even more preferably of at least –193°; the (–)-verbenone most preferred has an optical purity of –217° (c=10, ethanol).

The synthesis processes in question, in addition to being described individually in the Examples are also summarised in the accompanying scheme 1. As will be appreciates the majority of the novel derivatives according to the present invention can be prepared by way of the novel intermediates of formulae V, VI and VII, given below to which the invention therefore also relates.

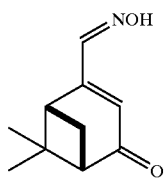

V

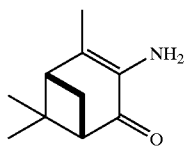

VI

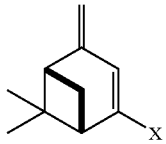

VII (wherein X=dimethylamino, diethylamino, pyrrolidino, piperidino and morpholino). Because (–)-verbenone constitutes a key intermediate in the synthesis of the novel derivatives of formula I, the present invention relates also to its use as an intermediate in the preparation thereof. The present invention relates also to the processes for the preparation of the compounds in question.

Those and other aspects of the present invention will be demonstrated more clearly by the following Examples, which are to be regarded purely as non-limiting illustrations thereof.

EXAMPLES

1) Starting from (–)-verbenone obtained by allyl oxidation of (–)-pinene, 10-hydroxyimino-2-pinen-4-one 2 was synthesised by nitrosation with isoamyl nitrite and metallic sodium in anhydrous diethyl ether at –5° C. and under a nitrogen atmosphere. Compound 2 was reacted:

a) with sodium hydroxide and zinc powder in a bi-phase water-ether system to give 3-amino-2-pinen-4-one 3 from which were obtained the salts 4 a–c (5-sulphosalicylate, tartrate, camphosulphonate), the amides 5 (with acyl, aliphatic, aromatic and heteroaromac chlorides in anhydrous diethyl ether in the presence of pyridine) and the ureas 6 (with alkyl isocyanates and aryl isocyanates in anhydrous benzene).

b) with compounds with reactive halogen (ethyl bromoacetate, chloroacetone, bromoacetonitrile, ethyl-4-chloroacetoacetate) in DMF in the presence of sodium bicarbonate at 75°, to yield the ethers 7 a–d. The acid 8 was obtained by alkaline hydrolysis of compound 7a.

2) Also starting from (–)-verbenone, there were prepared:

a) dienamines 9 a–e with an excess of dimethylamine, diethylamine, pyrrolidine, piperidine or morpholine in the presence of molecular sieves in the absence of solvents and at low temperature. The corresponding carboxamides 10 a–e were obtained from compounds 9 a–e with alkyl isocyanates and aryl isocyanates in anhydrous benzene and at elevated temperature.

b) α-keto ester 11 (70:30 mixture of cis-trans geometric isomers, the ketone group at α being present in enol form) with diethyl oxalate in anhydrous diethyl ether in the presence of metallic sodium.

c) benzylidene type 12 derivatives by reaction with aromatic and heteroaromatic aldehydes, in absolute ethanol in the presence of sodium hydroxide.

Apparatus

The melting points were determined using a Fisher-Johns apparatus. The IR spectra were recorded using a Perkin-Elmer 398 spectrophotometer, the $^1$H-NMR spectra with a Perkin-Elmer R-600 (60 MHz) using tetramethylsilane as the internal standard. Values of J in Hz.

Preparation of (−)-VERBENONE 1
(1S,5S)-4,6,6-Trimethylbicyclo[3.1.1]hept-3-en-2-one (−)-α-pinene (136.2 g, 1 mole) was oxidised by bubbling in $O_2$ in the presence of cobalt stearate (0.5 g), which is added portionwise, maintaining the temperature at approximately 5–55° C., for at least 50–60 hours. When the reaction was complete, the peroxide index was approximately 27–29%. After cooling to room temperature, the excess of peroxides was decomposed by adding to the reaction mixture an equal quantity of a hot aqueous solution (~50° C.) of 5% ferrous sulphate and 1% sulphuric acid; the peroxide index was approximately 0 within approximately 2 hours. The organic phase was then separated and washed 2–3 times with water until a pH of 5–6 is obtained. The non-reacted (−)-α-pinene was removed by column distillation at a temperature of approximately 100° C. and at a pressure of 20–25 mmHg ($2.6\times10^{-2}$–$3.3\times10^{-2}$ bar). The distillation residue was constituted by a mixture of terpenes which was characterized by oxygenated functions (alcohol, ketone and aldehyde functions). A Bertagnini reaction was then carried out by adding to the reaction mixture a solution containing sodium sulphite (120 g, 0.954 mole), while maintaining the temperature at 55–60° C. Because the pH of the mixture gradually moved to basic values, a 50% acetic acid solution was added until the pH is neutral. When the pH remained stable at ~7, the reaction, might be regarded as complete. The organic phase (containing the alcohols PINOCARVEOL, MIRTENOL, VERBENOL) was separated and the aqueous phase was counter-extracted 2–3 times with hexane. The aqueous solution was alkalinised to pH ~14 and then extracted with hexane, thus obtaining the fraction containing carbonyl products (MIRTENAL AND VERBENONE). The hexane extract, washed 2–3 times with water, was concentrated to obtain a high-boiling oily residue constituted to the extent of more than 80% by VERBENONE. The residue was dissolved with methanol; the methanol solution was cooled to −5 to −1° C. and, while maintaining this temperature, sodium borohydride was added until the MIRTENAL was undetectable (monitoring by TLC). The reduction was then stopped by the addition of a small amount of acetic acid, until the solution was neutral. The methanol solution was concentrated to ⅔ the volume, then diluted with water and extracted with hexane. The hexane solution was evaporated under vacuum and the residue is distilled at 80° C./1.5 mm Hg ($1.9\times10^{-3}$ bar) to give VRBENONE (25 g, yield 16.6%) with $[\alpha]_D^{2b}=-217°$ (c=10 in ethanol).

Synthesis of 10-Hydroxyimino-2-pinen-4-one 2
(10-Hydroxyiminoverbenone)
(1S,5S)-4-(Hydroxyimino)methyl-6,6-dimethylbicyclo-[3.1.1]hept-3-en-2-one Sodium in wire form (6.9 g, 0.3 mole) was added to an ice-cooled solution (5° C.), of (−)-verbenone (4.51 g, 0.3 mole) in anhydrous ether (180 ml). A solution of isoamyl nitrite (41 g, 0.35 mole) in anhydrous ether (100 ml) was immediately added dropwise, under an inert nitrogen atmosphere, to the reaction mixture. When the addition was complete, stirring and cooling were maintained for 4 hours. After introducing water (150 ml) into the reaction mixture, the aqueous phase, separated from the ether phase, was acidified with 1M HCl to pH=0 and extracted with ether. The combined ether extracts are dried over $MgSO_4$ and evaporated under vacuum: the residual viscous oil was crystallized from ether/petroleum ether. In order to obtain an analysis sample, subsequent crystallization was carried out: white solid, m.p. 164–165° C.

$C_{10}H_{13}NO$ [179.21] Calc.: C: 67.02; H: 7.31; N: 7.82; Found: C: 67.30; H: 7.44; N: 7.99; IR ($CHCl_3$): $cm^{-1}$ 3450, 3180, 1720, 1615; NMR ($CDCl_3$): δ 0.93 (s, 3H,$CH_3$); 1.44 (s, 3H, CH3); 1.5–1.9 (m, 1H, CH); 2.6–3.0 (m, 3H, $CH+CH_2$); 5.6 (d, J=1 Hz, 1H, CH=); 6.75 (d, J=1 Hz, 1H, CH=N); 11.3 (broad s, 1H, OH exchanged with $D_2O$).

Synthesis of 3-Amino-2-pinen-4-one (3-aminoverbenone) 3
(1S,5S)-3-Amino-4,6,6-trimethylbicyclo[3.1.1]hept-3-en-2-one Cold diethyl ether (300 ml) and activated zinc in powder form (100 g) were added, with vigorous stirring, to a solution of 10-hydroxyiminoverbenone 2 (71.68 g, 0.4 mole) in 4M sodium hydroxide (800 ml), which was cooled with an ice and salt bath. After a few minutes, there was a substantial development of heat: maintain stirring and cooling for 20–25 minutes. Subsequently, the aqueous phase and the ether phase are first separated from zinc by decantation and then from one another, extracting the aqueous phase again with ether. All the ether phases were combined, washed with water 3 times and then subjected to two alternative processes in order to obtain a pure product (a) or a highly purified product (b).

a) The ether phases were dried over $MgSO_4$ and evaporated u.v. (under vacuum) to give a reddish liquid which crystallizes slowly at low temperature (66.1 g, 84%).

b) The ether phases were extracted twice with 3M HCl (140 and 70 ml) and then discarded; the acidic aqueous phases, cooled with an ice bath, were made alkaline with 4M NaOH (210 ml) and extracted with ether. The combined ether phases, dried over $MgSO_4$, were chromatographed on Florisil, finally eluting again with diethyl ether.

After evaporation of the solvent u.v., a 7:1 petroleum ether:ether mixture was added, and then crystallization was performed at low temperature.

M.p. 45–46° C. (I crystallization); m.p. 47–48° C. (II and III crystallization) $C_{10}H_{15}NO$ Calc. C: 72.69; H: 9.15; N: 8.48; Found C: 72.48; H: 9.23; N: 8.41; IR ($CHCl_3$) $cm^{-1}$: 3430, 3350, 1665, 1585, $^1$H-NMR ($CDCl_3$) δ: 0.97 (s., 3H, $CH_3$), 1.47 (s., 3H, $CH_3$), 1.88 (s., 3H, $CH_3$), 1.98–2.88 (m, 4H, $CH_2$+2CH), 3.08–3.53 (broad s, 2H, $NH_2$, disappears as a result of the addition of $D_2O$).

Preparation of 3-Aminoverbenone-5-sulphosalicylate 4a

There was added to a cooled solution of 3-aminoverbenone 3 (24.73 g, 0.15 mole) in methanol (20 ml), a likewise cooled solution of finely pulverized 5-sulphosalicylic acid (38.13 g, 0.15 mole) in methanol (35 ml). After cooling to +4° C. and occasionally stirring for 3 hours the reaction mixture; diethyl ether was added until precipitation was complete. The solid (47.7 g, 83%) obtained was filtered dried in the air and recrystallized from dichloromethane:methanol (3:1). M.p. 209–210° C.

$C_{17}H_{21}NO_7S$ Calc. C: 53.25; H: 5.52; N: 3.65; Found C: 53.13; H: 5.52; N: 3.58; IR (KBr) cm$^{-1}$: 3640–3300, 3000–2500, 2590, 1675, 1660–1640; $^1$H-NMR [(CD$_3$)$_2$SO) 0.95 (s., 3H, CH$_3$), 1.45 (s., 3H, CH$_3$), 1.9–2.2 (m, 1H, CH), 2.08 (s., 3H, CH3), 6.8–7.10 (m., 1H, H-5 phenyl), 7.7–7.95 (m., 1H, H-6 phenyl), 8.07–8.25 (m., 1H, H-2 phenyl) 10 (broad s, 5H, NH$_3^+$+COOH+OH, disappeared with D$_2$O).

*The position of the signal might vary as a function of the concentration.

Preparation of 3-Aminoverbenone L-(+)Tartrate Monohydrate 4b

A solution of 3-aminoverbenone (8.26 g, 50 mmoles) in diethyl ether (75 ml)/petroleum ether (75 ml) was added dropwise under stirring to an ice-cooled solution of L-(+)-tartaric acid (7.50 g, 50 mmoles) in methanol (35 ml). After stirring and cooling for one hour the reaction mixture was maintained at ~18° C. overnight. The separated pure solid was filtered, washed with ether (12.2 g, 73%) and recrystallized from methanol:ether:petroleum ether (1:1:1). M.p. 129–131° C.

$C_{14}H_{23}NO_N$ Calc. C: 50.45; H: 6.95; N: 4.20; Found C: 50.31; H: 6.89; N: 4.30; UV (H$_2$O), $\lambda_{max}$: 258 nm ($\epsilon$=3500); IR (KBr) cm$^{-1}$: 3500–3160, 3000–2500, 2540, 1725, 1675–1655; $^1$H-NMR [(CD$_3$)$_2$SO)] δ: 0.89 (s., 3H, CH3), 1.43 (s., 3H, CH$_3$), 1.82 (s.; 3H, CH$_3$), 1.90–3.05 (m., 4H. CH$_2$+2CH), 4.32 (s., 2H, CH—CH tartar.), 6.62 (broad s, 8H, NH$_3$+2OH+COOH+H$_2$O, disappeared with D$_2$O).

Synthesis of 3-Aminoverbenone: (1S)-(+)-10-Camphosulphonate 4c

A solution of monohydrated (1S)-(+)-10-camphosulphonic acid (2.5 g, 10 mmoles) in methanol (15 ml) was added to an ice-cooled solution of 3 (1.65 g, 10 mmoles) in methanol (15 ml). The resultant solution was stirred for 1 hour at room temperature. After evaporation of the solvent, the solid residue was recrystallized from methylene chloride:ether 1:3. M.p. 150–152° C. (70%).

$C_{20}H_{31}NO_5S$ Calc. C: 60.43; H: 7.86; N: 3.52; Found C: 60.29; H: 7.79; N: 3.54; IR (CHCl$_3$), cm$^{-1}$: 2700–2400, 1735, 1685, 1655, 1285, 1170, 1035; $^1$H-NMR (CDCl$_3$) δ 0.80 (s., 3H, CH$_3$), 1.05 (s., 6H, 2CH$_3$), 1.51 (s, 3H, CH$_3$), 2.25 (s., 3H, CH$_3$), 1.25–3.02 and 3.10–3.60 (various multiplets, 13H, 3CH+5CH$_2$) 7.43–8.3 (broad s, 3H, NH$_3^+$ disappeared with D$_2$O).

General Procedure for the Synthesis of the Amides 5 of 3-Aminoverbenone

N-[(1S,5S)-4,6,6-Trimethyl-2-oxobicyclo[3.1.1]hept-3-en-3-yl]arylcarboxamides

A suitable acyl chloride was added at room temperature to a stirred solution of 3 (1.65 g, 10 mmoles) in anhydrous ether (20 ml) and anhydrous pyridine (3 ml). After stirring the mixture for 3 hours, the reaction solvent was evaporated under vacuum. The resultant residue was treated with water (50 ml) and extracted with ether. The combined ether phases were washed with 2M HCl (15 ml) and 1M NaHCO$_3$ (15 ml), dried over magnesium sulphate and evaporated under vacuum: the residue was recrystallized from a suitable solvent

Example No. 1

Synthesis of N-[(1S,5S)-4,6,6-Trimethyl-2-oxobicyclo-2-[3.1.1]-hept-3-en-3-yl]-2-acetoxybenzamide 5 [Ar=2-(OCOCH$_3$)C$_6$H$_1$]

Acetylsalicylic acid chloride (1.99 g, 10 mmoles) was added at room temperature, with stirring, to a solution of 3 (1.65 g, 10 mmoles) in anhydrous ether (20 ml) and anhydrous pyridine (3 ml). The reaction mixture was stirred for 3 hours at room temperature and the reaction solvent was evaporated under vacuum. The residue was taken up with water (50 ml) and extracted with ether. The combined ether phases were washed with 2M HCl (15 ml) and 1M NaHCO$_3$ (15 ml), dried over MgSO$_4$ and evaporated u.v.: the residue was recrystallized from ether-petroleum ether (1:2). M.p. 87–89° C. (72%).

$C_{19}H_{21}NO_4$ Calc. C: 69.70; H: 6.47; N: 4.28; Found C: 69.57; H: 6.51; N: 4.21; IR (KBr) cm$^{-1}$: 3325, 1760, 1660; $^1$H-NMR (CDCl$_3$) δ 1.08 (s., 3H, CH$_3$), 1.53 (s., 3H, CH$_3$), 2.03 (s., 3H, CH$_3$CO), 2.45 (s., 3H, CH$_3$), 1.66–3.20 (various multiplets, 4H, 2CH+CH$_2$) 7.06–7.75 and 7.80–8.25 (m., 5H, C$_6$H$_4$+NH).

The amide NH signal showed in a broad singlet at approximately δ 8.10, partially superimposed on the multiplet of the aromatic protons, and disappeared as a result of deuteration with CF$_3$COOD.

General Procedure for the Synthesis of the Ureas 6 of 3-Aminoverbenone

N-(Alkyl or Aryl)-N'-[(1S,5S)-4,6,6-trimethyl-2-oxobicyclo [3.1.1]hept-3-yl]ureas Alkyl or aryl isocyanate (10 mmoles) was added at room temperature to a solution of 3 (1.65 g, 10 mmoles) in anhydrous benzene (15 ml). The reaction mixture was maintained under stirring at room temperature for 15 minutes and then heated at 65° C. for two hours. After evaporation of the solvent, the residue constituted by the ureas was recrystallized from a suitable solvent

Example No. 2

Synthesis of N-(Phenyl)-N'-[(2S,5S)-4,6,6trimethyl-2-oxobicyclo-[3.1.1]hept-3-en-3-yl]urea 6 (R$_1$= C$_6$H$_5$)

Phenyl isocyanate (1.19 g, 10 mmoles) was added at room temperature to a solution of 3 (1.65 g, 10 mmoles) in anhydrous benzene (15 ml). The reaction mixture was maintained under stirring at room temperature for 15 minutes and was then heated at 65° C. for two hours. By evaporation of benzene under vacuum, a viscous residue was obtained which is crystallized from ether-petroleum ether (3:1). M.p. 134–135° C. (65%).

$C_{17}H_{20}N_2O_2$ Calc. C: 71.81; H: 7.09; N: 9.85; Found C: 71.87; H: 7.10; N: 9.87; IR (CHCl$_3$) cm$^{-1}$: 3360, 1660,1635; $^1$H-NMR (CDCl$_3$) δ: 1.07 (s., 3H, CH3), 1.51 (s., 3H, CH$_3$), 2.08 (s., 3H, CH$_3$), 2.05–3.04 (m. 4H, 2CH+CH$_2$) 6.80–7.60 (m, 6H, C$_6$H$_5$+=C—NH—CO) 7.80–8.15 (s, broadened, 1H, C$_6$H$_4$-NH).

The two urea NH signals disappeared as a result of deuteration with D$_2$O.

General Procedure for the Synthesis of the Ethers 7 a–d

Sodium bicarbonate (0.81 g, 10 mmoles) aid the alkylating reagent (Br—CH$_2$—COOC$_2$H$_5$, Cl—CH$_2$—CO—CH$_3$, Br—CH$_2$CN, Cl—CH$_2$—CO—CH$_2$—COOC$_2$H$_5$, 10 mmoles) were added to a solution of 2 (17.9 g, 10 mmoles) in non-anhydrous DMF (15 ml). The resultant suspension was heated for three hours at 75–80° C., diluted with H$_2$O (200 ml) and extracted with ether. The combined ether phases were washed five times with water, dried with MgSO$_4$ and, evaporated at reduced press. The resultant residue was chromatographed on Florisil (eluant ether) and

Example No 3

Synthesis of 10-[[(Ethoxycarbonylmetyl]oxyimino] verbenone 7a

Ethyl 2-[[[(1S,5S)-6,6-Dimethyl-4-oxobicyclo[3.1.1]hept-2-en-2-yl]methyl]imino]oxyacetate Sodium bicarbonate (0.85 g, 10 mmoles) and ethyl bromoacetate (1.67 g, 10 mmoles) were added to a solution of 10-hydroxyiminoverbenone 2 (1.79 g, 10 mmoles) in nonanhydrous DMF (15 ml); the resultant suspension was heated for three hours at 75–80° C., diluted with $H_2O$ (200 ml) and extacted with ether. The combined ether phases were washed with $H_2O$ five times, dried over $MgSO_4$ and evaporated at reduced pressure. The residual liquid was chromatographed on Florisil (eluant ether) and subjected to bubble distillation (170–175° C./0.1 mmHg)(1.3×10$^{-4}$ bar) (85%).

$C_{14}H_{19}NO_4$ Calc. C: 63.38; H: 7.22; N: 5.28; Found C: 63.22; H: 7.30; N: 5.40; IR (CHCl$_3$) cm$^{-1}$: 1735, 1715, 1555, 1270, 1050; $^1$H-NMR (CDCl$_3$) δ: 0.94 (s, 3H, CH$_3$), 1.28 (t, partially superimposed, J=7 Hz, 3H, CH$_3$), 1.43 (s, 3H, CH$_3$), 1.62–1.98 (m, 1H, CH), 2.58–3.02 (m, 3H, CH$_2$+CH), 4.25 (q, J=7 Hz, 2H, CHO), 4.99 (s, 2H, CH$_2$), 5.66 (d, J=2 Hz, 1H, CH═), 6.62 (d, J=2 Hz 1H, CH═N).

Synthesis of 2-[[[(1S,5S)-6,6-Dimethyl-4-oxobicyclo[3.1.1]hept-2-en-2 -yl]methyl]imino] oxyacetic Acid 8

7a (2.65 g, 10 mmoles) dissolved in diethyl ether (15 ml) is added under stirring to an ice-cooled solution of KOH (0.56 g, 10 mmoles) in methanol (15 ml). The reaction mixture was stirred for eight hours at room temperature and, after evaporation of the solvents at reduced pressure, the residue is treated with brine $H_2O$ (50 ml). The aqueous phase was subsequently washed twice with ether, acidified with 2M HCl to pH=O and extracted with ether. The combined ether phases were dried over $MgSO_4$ and evaporated under vacuum (u.v.) to give a viscous liquid which was chromatographed on Florisil (eluants:dichloromethane:ether 1:4) and crystallized from dichloromethane/petroleum ether 1:4. M.p. 134–135° C. (65%).

$C_{12}H_{15}NO_4$ Calc. C: 60.75; H: 6.37; N: 5.90; Found C: 60.95; H: 6.45; N: 5.96; IR (CHCl$_3$) cm$^{-1}$: 3500–3100, 1715, 1615, 1560, 1240, 1050; $^1$H-NMR (CDCl$_3$) δ: 0.94 (s, 3H, CH$_3$), 1.44 (s, 3H, CH$_3$), 1.58–2.02 (m, 1H, CH), 2.55–3.05 (m, 3H, CH$_2$+CH), 5.01 (s, 2H, CH$_2$O), 5.67 (s, 1H, CH═), 6.60 (s, 1H, CH═N), 10.84 (s, 1, COOH, exchanged with $D_2O$).

General Procedure for the Synthesis of the Dienamines 9 a–e (1S,5S)-2-Cycloalkyl (or Dialkyl)amino-6.6-dimethyl-4-methylenebicyclo[3.1.1]hept-3-enes Molecular sieves (2 g) and (–)-verbenone (3.0 g, 20 mmoles) were added to the freshly distilled pure secondary amine (9 ml) cooled with an ice bath After being maintained at a low temperature in a refrigerator for 10 hours and shaken occasionally by hand, the reaction mixture was diluted with anhydrous ether (50 ml) and filtered rapidly to eliminate the molar sieves. After evaporation of the ether and the excess amine under vacuum, the liquid residue was subjected to bubble distillation. The products obtained were sensitive to heat (partial decomposition may be observed during their distillation) and are kept away from light, moisture and oxygen.

subjected to bubble distillation if it was liquid or from a suitable solvent if it was solid.

Example No. 4

Preparation of the Pyrrolidinodienamine of (–)-Verbenone 9c (1S,5S)-6,6-Dimethyl-4-methylene-2-pyrrolidinobicyclo[3.1.1]hept-2-ene Pure (–)-verbenone (3 g, 20 mmoles) was added, under string at low temperature, to pure pyrrolidine (9 ml) to which molecular sieves (2 a) have been added. The reaction mixture was maintained at +4° C. (in a refrigerator) for, 10 hours and occasionally stirred by hand. After the addition of anhydrous ether (50 ml), the whole was filtered and concentrated under vacuum, washing the sieves with anhydrous ether. After evaporation of the solvent and the pyrrolidine u.v., the residual red viscous liquid was subjected to bubble distillation (105–110° C./0.4 mmHg)(5.2×10$^{-4}$ bar) to give a yellow oil (2.5 g, yield 61.5%) which tends to polymerize during distillation and was sensitive to oxygen, moisture and light $C_{14}H_{21}N$ Calc. C: 82.70; H: 10.41; N: 6.89; Found: C: 82.50; H: 10.56; N: 6.57; IR (CHCl$_3$): 1585 cm$^{-1}$; NMR (CDCl$_3$): δ 0.94 (s, 3H, CH$_3$), 1.38 (s, 3H, CH$_3$) 1.5–2.07 (m, 5H, 2CH$_2$pyrr+CH), 2.4–2.7 (m, 3H, CH$_2$+CH), 2.97–3.30 (m, 4H, 2CH$_2$N), 4.2 and 4.3 (q$_{AB}$, J=2 Hz, 2H,=2CH$_2$), 4.72 (near s, 1H, ═CH).

General Procedure for the Synthesis of the Dienamine Carboxamides 10 a–e

Substituted N-(Alkyl or aryl) [[(1S,5S)-4-dialkyl (or Cycloalkyl)amino]-6,6-dimethyl-bicyclo[3.1.1]hept-3en-2-ylidene]carboxamides An equimolar solution (10 mmoles) of enamine and alkyl or aryl isocyanate in anhydrous benzene (20 ml) was stirred at room temperature for 1 hour and then heated at 60° C. for one hour. After evaporation of the solvent, the residue was dissolved in dichloromethane and the resultant solution was extacted with 3M hydrochloric acid (10 ml×2). The acidic aqueous phase, separated from the organic phase, was made completely alkaline with 4M sodium hydroxide and extracted with dichloromethane. After the usual treatments, the organic phase furnished solid residues or viscous liquids which were recrystallized from suitable solvents.

Example No. 5

Synthesis of 2-[(1S,5S)-6,6-Dimethyl-4-pyrrolidinobicyclo[3.1.1]hept-3-en-2-ylidene] acetanilide 10c (R═C$_6$H$_5$)

A solution of the Dienamine 9c (2.03 g, 10 mmoles) and phenyl isocyanate (1.2 g. 10 mmoles) in anhydrous benzene (20 ml) was stirred at room temperature for 1 hour and subsequently heated at 60° C. for one hour. The solvent was evaporated u.v. and the residue was dissolved in dichloromethane. The organic phase was extracted twice (10 ml) with 3M hydrochloric acid and then eliminated. The acidic phase, which was rendered alkaline with 4M sodium hydrate, was extracted with dichloromethane, dried and evaporated under vacuum to give a viscous liquid which, by crystallization from dichloromethane:petroleum ether (1:1), afforded a yellow solid (1.6 g, yield: 50%); m.p. 202–204° C.

$C_{21}H_{20}N_2O$ Calc. C: 78.22; H: 8.13; N: 8.69; Found: C: 78.10; H: 8.05; N: 8.50; IR (CHCl$_3$): cm$^{-1}$ 3440, 1640; NMR (CDCl$_3$) δ: 0.92 (s, 3H, CH$_3$), 1.42 (s, 3H, CH$_3$) 1.56–2.06 (m, 5H, 2CH$_2$pyrr+CH) 3.06–3.46 (m, 4H, 2CH$_2$N), 5.04 (s, 1H, CH) 6.26 (quasi s, 1H, CH—CO) 6.76–7.44 and 7.50–7.80 (m, 5H, C$_6$H$_5$) 9.30 (s, 1H, NH exchanged with $D_2O$).

Synthesis of 10-(Ethyloxalyl)verbenone
Ethyl 3-[(1S,5S)-6.6-dimethyl]-4-oxobicyclo[3.1.1]hept-2-en-2-yl]-2-oxopropanoate 11

Sodium wires (0.69 g, 30 mmoles) are added to a solution of (−)-verbenone (4.51 g, 30 mmoles) and diethyl oxalate (4.38 g, 30 mmoles) in anhydrous diethyl ether (80 ml). The resultant reaction mixture was stirred for 5 hours at room temperature and then petroleum ether (20 ml) and water (30 ml) are added. The aqueous phase (basic), separated from the organic phase, was acidified with 1M hydrochloric acid aid extracted with ether. The combined ether phases are dried over $MgSO_4$ and evaporated under vacuum to give a red viscous liquid (4 g) (1) from which a yellow crystalline product (2) was separated by crystallization from diethyl-ether-petroleum ether (1:2) (2.5 g, yield 33%), m.p. 101° C.

$C_{14}H_{18}O_4$ Calc.: C: 67.18; H: 7.25; Found: C: 6724; H: 7.43; IR ($CHCl_3$): 3450, 1700, 1660, 1645, 1610 cm$^{-1}$; NMR ($CDCl_3$) δ: 0.88 (s, 3H, $CH_3$) 1.38 (t, J=7 Hz, 3H, $CH_3CH_2$) 1.50 (s, 3H, CH3) 1.9–2.3 (m, 1H, CH) 2.6–3.1 and 3.74.0 (2m, 3H, $CH+CH_2$) 4.38 (q, J=7 Hz 2H $CH_2CH_3$), 6.10 (s, 1H,=CH) 6.70 and 6.90 (2 near s, 1H, CH), 8.0–8.7 (broad s, 1H, OH exchanged with $D_2O$).

(1) 70:30 mixture of cis-trans isomers (ratio deduced from the $^1$H-NMR spectrum), the ketone carbonyl in the a position relative to the ester group being in the enol form.

(2) The substance concerned was one of the isomers, probably the trans isomer.

General Procedure for the Synthesis of the (1S,5S)-4-(2-Aryl or 2-heteroayl)vinyl-6,6-dimethylbicyclo[3.1.1]hept-3-en-2-ones 12

(−)-verbenone (1.5 g, 10 mmoles) and a suitable aromatic or heteroaromatic aldehyde (10 mmoles) were added to a stirred solution of sodium hydroxide (0.4 g, 10 mmoles) in absolute ethanol (35 ml). After stirring the reaction mixture overnight, the solvent was evaporated u.v. The residue was treated with water (80 ml) and extracted with ether (or dichloromethane). The organic phases were dried over $MgSO_4$ and evaporated u.v. to give viscous liquids or solids which were purified, respectively, by bubble distillation under a high vacuum or by crystallization on from suitable solvents.

Example No. 6

Synthesis of (1S,5S)-4-[(Benzylidene)methyl]-6,6-dimethylbicyclo[3.1.1]hept-3en-2-one 12
(Ar=$C_6H_5$)

(−)-verbenone (1.5 g, 10 mmoles) and benzaldehyde (1.06 g, 10 mmoles) were added to a stirred solution of NaOH (0.4 g, 10 mmoles) in absolute ethanol (35 ml). After stirring the reaction mixture overnight, the solvent was evaporated u.v. The residue was treated with water (50 ml) and ted with ether. The ether phases were dried over $MgSO_4$ and evaporated u.v. to give a yellowish viscous liquid which was subjected to bubble distillation at 180–185° C./0.8 mmHg ($10^{-3}$ bar)(yield 75%).

$C_{17}H_{18}O$ Calc. C: 85.67; H: 7.61; Found: C: 85.57; H: 7.53; IR ($CHCl_3$) cm$^{-1}$: 1655, 1612; $^1$H-NMR ($CDCl_3$) δ: 1.03 (s, 3H, $CH_3$), 1.59 (s, 3H, $CH_3$), 1.93–2.28 and 2.52–332 (m, 4CH, $CH_2$+2CH), 5.95 (near s, 1H, H-3, CH=), 7.08 (s, 2H, CH=CH—$C_6H_5$), 7.20–7.70 (m, 5H, $C_6H_5$).

Example No. 7

Comparative Test

The anti-inflammatory activity of 3-amino-(−)-verbenone-5-sulphosalicylate was compared with that of (−)-verbenone in accordance with methods described in the literature (C. A. WINTER et al. Carrageenin induced edema in hind paw of the rat as an assay for antinflammatory drugs. Proc. Soc. Exp. Biol. Med. 111, 544, 1962. CURVOISIER et al. Action of chlorpromazine on the edema produced by dextran in rats. Arch. Inter. Pharmacodynamie, 102, 33–54, 1955. B. B. NEWBOULD) Chemotherapy of arthritis induced in rats by microbacterial adjuvant. Brit. J. Pharmacol. 21, 127–135, 1963. J. V. HURLEY et al. Reagin-Like antibodies in animals immune to helminth parasites. Nature (Lond.) 204, 91, 1964. ROTHKOPF et al. Arzneimittel Forschung 26, 225–235, 1976. C. A. WINTER et al. Antitussive compounds: testing methods and results. J. Pharmacol. Exp. Ther. 112, 99, 1954. G. OSTERLOH Arzneimittel Forschung, 16, 901, 1966); the results are given hereinafter in schematic form.

1. Carrageenin-induced Oedema in the Rat per OS
    Parameter: percentage volumetric inhibition; maximum effect 120 minutes after administration:
    (−)-verbenone (200 mg/kg)=63%
    3-amino-(−)-verbenone-5-sulphosalicylate (200 mg/kg)= 78%

2. Carrageenin-induced Oedema in the Rat by the Intraperitoneal Route
    Parameter: percentage volumetric inhibition; maximum effect 120 minutes after administration:
    (−)-verbenone (120 mg/kg)=48%
    3-amino-(−)-verbenone-5-sulphosalicylate (120 mg/kg)= 67%

3 Adjuvant Arthritis in the Rat by the Intraperitoneal Route
    Parameter: percentage inhibition of the volumetric increase of the lower limbs; day "28":
    (−)-verbenone (60 mg/kg)=39%
    3-amino-(−)-verbenone-5-sulphosalicylate (60 mg/kg)= 64%

4. Turpentine-induced Pleurisy in the Rat by the Intraperitoneal Route
    Parameter: percentage inhibition of the volume of exudate and of leukocyte migration:
    (−)-verbenone (60 mg/kg)=49%
    3-amino-(−)-verbenone-5-sulphosalicylate (60 mg/kg)= 68%

5. Carrageenin-induced Pleurisy in the Rat per OS
    Parameter: percentage inhibition of the volume of exudate:
    (−)-verbenone (180 mg/kg)=46%
    3-amino-(−)-verbenone-5-sulphosalicylate (180 mg/kg)= 72%

6. Carrageenin-induced Pleurisy in the Rat by the Intraperitoneal Route
    Parameter: percentage inhibition of the volume of exudate:
    (−)-verbenone (25 mg/kg)=48%
    3-amino-(−)verbenone-5-sulphosalicylate (25 mg/kg)= 64%

7. Acrolein-induced Aerosol in the Guinea Pig by the Intraperitoneal Route
    Parameter: inflammation of the upper, middle, lower airways: scores (double blind):
    (−)-verbenone (30 mg/kg)=24
    3-amino-(−)-verbenone-5-sulphosalicylate (30 mg/kg)= 18

8. Adverse Gastric Activity in the Rat per OS
    Parameter: evaluation of adverse gastric action according to Osterloh
    (−)-verbenone (360 mg/kg)=2
    3-amino-(−)-verbenone-5-sulphosalicylate (360 mg/kg)= 0.85

Conclusions

The following conclusions may be drawn from the tests indicated above: 3-amino-(−)-verbenone-5-sulphosalicylate exhibits an anti-inflammatory activity which is higher than that of (−)-verbenone to an extent varying approximately between 23 and 64%, depending on the method used (Examples 1–7), and also a substantially lower adverse gastric activity (Example 8).

N. B. It should be emphasised in this connection that the results of Examples 1–6 have been given as a percentage of volumetric inhibition; Examples 7 and 8, however, indicate inflammation and adverse gastric action of a residual nature after treatment.

What is claimed is:

1. A compound having the formula

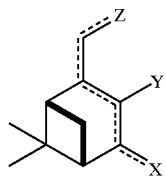

I wherein, when X=O

Z=H, =CHAr, =C(OH)COOEt, =NOR;

Y=H, $NH_2$, $NH_3^+X_1^-$, NHCOAr, NHCOR, NHCONHR, NHCONHAr;

$X_1^-$=pharmaceutically acceptable anion;

Ar=aryl selected from among the group consisting of: phenyl, 4chlorophenyl, 2-furyl, 2-thienyl, 2 hydroxyphenyl and 2-acetophenyl;

R=H, $C_1$–$C_4$ alkyl, $C_4$–$C_6$ cycloalkyl, $CH_2COOH$, $CH_2COOEt$, $CH_2COCH_3$, $CH_2CN$, $CH_2COOCH_2COOEt$, $CH_2C_6H_5$;

with the proviso that when X=O ad Y=HZ is other than H;

and when X=dimethylamino, diethylamino, pyrrolidino, piperidino, or morpholino;

Y=H; Z=EL CONHAr, CONHR; Ar=aryl; R=H, $C_1$–$C_4$ alkyl, $C_4$–$C_6$ cycloalkyl; with the proviso that when Z=H, X is other than pyrrolidino.

2. A compound according to claim 1 having the formula

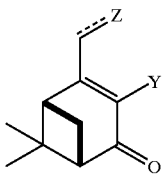

II wherein:

when Y=H Z==CHAr, =C(OH)COOEt, =NOR; or, alternatively, when Z=H, Y=$NH_2$, $NH_3^+X_1^-$, NHCOAr, NHCOR, NHCONHR, and wherein:

$X_1^-$=5-sulphosalicylate, tartrate, 10-camphosulphonate;

Ar=phenyl 4-chlorophenyl, 2-furyl, 2-thienyl, 2-hydroxyphenyl, 2-acetoxyphenyl;

R=H, $C_1$–$C_4$ alkyl $C_4$–$C_6$ cycloalkyl, $CH_2COOH$, $CH_2COOEt$, $CH_2COCH_3$, $CH_2CN$, $CH_2COCH_2COOEt$, $CH_2C_6H_5$.

3. A compound according to claim 1 having the formula

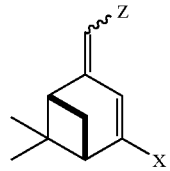

III wherein:

X=dimethylamino, diethylamino, pyrrolidino, piperidino or morpholino;

Z=H, CONHAr, —CONHR;

Ar=phenyl;

R=H, methyl cyclohexyl;

with the proviso that when when Z=H, X is other than pyrrolidino.

4. A compound having the formula

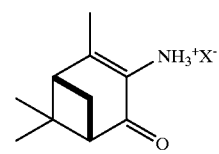

IV wherein $X_1^-$ is a pharmaceutically acceptable anion.

5. A compound according to claim 4 wherein the pharmaceutically acceptable anion is selected from 5-sulphosalicylate, tartrate, 10-camphosulphonate.

6. 3-amino-(−)-verbenone-5-sulphosalicylate.

7. A pharmaceutical composition containing at least one compound according to claims 1–6 as active ingredient together with the normal excipients and/or co-adjuvants.

8. A compound having the formula

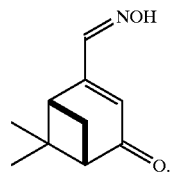

V

9. A compound having the formula

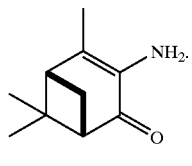

VI

10. A compound having the formula

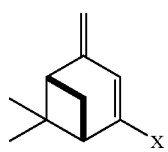

VII wherein X=dimethylamino, diethylamino, pyrrolidino, piperidino and morpholino.

11. A process for the preparation of a compound according to claim 4 comprising the following steps:
   a) nitrosation of the methyl in the 4 position of (−)-verbenone to give 10-hydroxyiminoverbenone;
   b) reduction of 10-hydroxyiminoverbenone to give 3-aminoverbenone;
   c) treatment of 3-aminoverbenone with a pharmacologically acceptable organic acid.

12. A process according to claim 11, characterized in that the pharmacologically acceptable organic acid is selected from 5-sulphosalicylic acid, L-(+)-tartaric acid and (1S)-(+)-10-camphosulphonic acid.

13. A process according to claim 11, characterized in that the nitrosation of the methyl in the 4 position of (−)-verbenone is carried out by means of isoamyl nitrite in the presence of metallic sodium.

14. A process according to claim 11, characterized in that the reduction of the 10-hydroxyiminoverbenone is carried out by means of zinc in the presence of sodium hydroxide.

15. A method for preparing a pharmaceutical compound wherein the formula of a composition is:

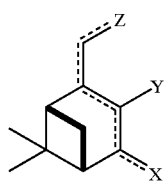

I when X=O

Z=H, =CHAr, =C(OH)COOEt, =NOR;

Y=H, $NH_2$, $NH_3^+X_1^-$, NHCOAr, NHCOR, NHCONHR, NHCONHAr;

$X_1^-$=pharmaceutically acceptable anion;

Ar=aryl selected from among the group consisting of phenyl, 4-chlorophenyl, 2-furyl, 2-thienyl, 2 hydroxyphenyl and 2-acetophenyl;

R=H, $C_1$–$C_4$ alkyl, $C_4$–$C_6$ cycloalkyl, $CH_2COOH$, $CH_2COOEt$, $CH_2COCH_3$, $CH_2CN$, $CH_2COOCH_2COOEt$, $CH_2C_6H_5$;

with the proviso that when X=O and Y=H, Z is other than H;

and when X=dimethylamino, diethylamino, pyrrolidino, piperidino, or morpholino:

Y=H; Z=H, CONHAr, CONHR; Ar=azyl; R=H, $C_1$–$C_4$ alkyl, $C_4$–$C_6$ cycloalkyl;

with the proviso that when Z=H, X is other than pyrrolidino, and includes a step in which said composition is used in the preparation of said pharmaceutical compound.

16. The method as rectied in claim 15, wherein said pharmaceutical composition has anti-inflammatory activities.

17. The method as rectied in claim 15, wherein said pharmaceutical composition has anti-muco-regulatory activities.

18. A method for making a compound, said compound having the formula:

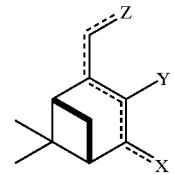

I when X=O

Z=H, =CHAr, =C(OH)COOEt, =NOR;

Y=H, $NH_2$, $NH_3^+X_1^-$, NHCOAr, NHCOR, NHCONHR, NHCONHAr;

$X_1^-$=pharmaceutically acceptable anion;

Ar=aryl, selected from among the group consisting of: phenyl, 4-chlorophenyl, 2-furyl, 2-thienyl, 2 hydroxyphenyl and 2-acetophenyl;

R=H, $C_1$–$C_4$ alkyl, $C_4$–$C_6$ cycloalkyl, $CH_2COOH$, $CH_2COOEt$, $CH_2COCH_3$, $CH_2CN$, $CH_2COOCH_2COOEt$, $CH_2C_6H_5$;

with the proviso that when X=O and Y=H, Z is other than H;

and when X=dimethylamino, diethylamino, pyrrolidino, piperidino, or morpholino;

Y=H; Z=H, CONHAr, CONHR; Ar=azyl; R=H, $C_1$–$C_4$ alkyl, $C_4$–$C_6$ cycloalkyl;

with the proviso that when Z=H, X is other than pyrrolidino, including a step wherein a composition having the formula selected from the group consisting of;

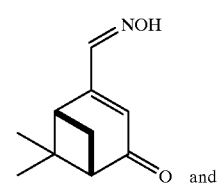

V and

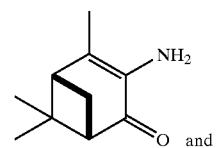

VI and

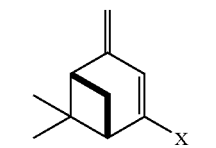

VII is used as an intermediate in the preparation of said compound.

19. A method for making a compound, wherein said compound has the following formula:

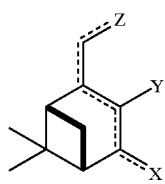

I when X=O
  Z=H, =CHAr, =C(OH)COOEt, =NOR;
  Y=H, $NH_2$, $NH_3^+X_1^-$, NHCOAr, NHCOR, NHCONHR, NHCONHAr;
  $X_1^-$=pharmaceutically acceptable anion;
  Ar=aryl, selected from among the group consisting of phenyl, 4-chlorophenyl, 2-furyl, 2-thienyl, 2 hydroxyphenyl and 2-acetophenyl;
  R=H, $C_1$–$C_4$ alkyl, $C_4$–$C_6$ cycloalkyl, $CH_2COOH$, $CH_2COOEt$, $CH_2COCH_3$, $CH_2CN$, $CH_2COCH_2COOEt$, $CH_2C_6H_5$;
  with the proviso that when X=O and Y=H, Z is other than H;
and when X=dimethylamino, diethylamino, pyrrolidino, piperidino, or morpholino;
  Y=H; Z=H CONHAr, CONHR; Ar=aryl, R=H $C_1$–$C_4$ alkyl, $C_4$–$C_6$ cycloalkyl; with the proviso that when Z=H, X is other than pyrrolidino,
  including a step in which (−)-verbenone is used as an intermediate in the preparation of said compound.

20. The method of making a pharmaceutical compound as recited in claim 15, wherein the formula of said composition is:

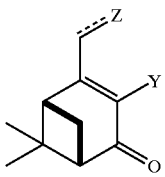

II when Y=H Z==CHAr, =C(OH)COOEt, =NOR; or, alternatively,
when Z=H, Y=$NH_2$, $NH_3^+X_1^-$, NHCOAr, NHCOR, NHCONHR; and wherein:
  $X_1^-$=5-sulphosalicylate, tartrate, 10-camphosulphonate;
  Ar=phenyl, 4-chlorophenyl, 2-furyl, 2-thienyl, 2-hydroxyphenyl, 2-acetoxyphenyl;

R=H, $C_1$–$C_4$ alkyl, $C_4$–$C_6$ cycloalkyl, $CH_2COOH$, $CH_2COOEt$, $CH_2COCH_3$, $CH_2CN$, $CH_2COCH_2COOEt$, $CH_2C_6H_5$.

21. The method of making a pharmaceutical compound as recited in claim 15, wherein the formula of said composition is:

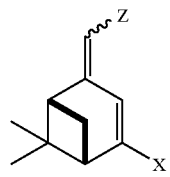

III

X=dimethylamino, diethylamino, pyrrolidino, piperidino or morpholino;
Z=H, CONHAr, —CONHR;
Ar=phenyl;
R=H, methyl, cyclohexyl;
with the proviso that when when Z=H, X is other than pyrrolidino.

22. A method of making a pharmaceutical compound, wherein the formula of a composition is

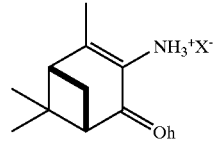

IV wherein $X_1^-$ is a pharmaceutically acceptable anion and includes a step wherein said composition is used in the preparation of said pharmaceutical compound.

23. The method of making a pharmaceutical compound as recited in claim 22 wherein the pharmaceutically acceptable anion is selected from the group consisting of: 5-sulphosalicylate, tartrate, and 10-camphosulphonate.

24. A method of making a pharmaceutical compound including the step of using 3-amino-(−)-verbenone-5-sulphosalicylate in the preparation of said pharmaceutical compound.

25. The compound recited in claim 1, wherein when X=dimethylamino, diethylamino, pyrrolidino, piperidino, or morpholino, Ar=phenyl.

* * * * *